United States Patent [19]

Drabek et al.

[11] 4,336,266
[45] Jun. 22, 1982

[54] INSECTICIDAL 2,2-DIMETHYL-3-(2',2'-DIHALOVINYL)-CYCLOPROPANE CARBOXYLIC ACID 3-HALOPHENOXY-α-VINYLBENZYL ESTERS

[75] Inventors: Jozef Drabek, Oberwil; Peter Ackermann, Reinach; Saleem Farooq, Ettingen; Laurenz Gsell, Basel; Odd Kristiansen, Möhlin, all of Switzerland

[73] Assignee: Ciba-Geigy Corporation, Ardsley, N.Y.

[21] Appl. No.: 240,334

[22] Filed: Mar. 3, 1981

Related U.S. Application Data

[63] Continuation-in-part of Ser. No. 84,954, Oct. 15, 1979, abandoned.

[30] Foreign Application Priority Data

Nov. 26, 1978 [CH] Switzerland ............ 11077/78
Sep. 11, 1979 [CH] Switzerland ............ 8504/79

[51] Int. Cl.³ .............. C07C 69/743; A01N 53/00
[52] U.S. Cl. .................... 424/305; 560/124
[58] Field of Search .............. 560/124; 424/305

[56] References Cited

U.S. PATENT DOCUMENTS 4,024,163  5/1977  Elliott ............ 260/347.4

Primary Examiner—Michael Shippen
Attorney, Agent, or Firm—Frederick H. Rabin

[57] ABSTRACT

The invention relates to vinylcyclopropanecarboxylic acid 3-phenoxy-α-vinylbenzyl esters of the formula

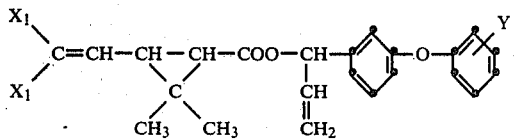

wherein each of $X_1$ and Y is fluorine, chlorine or bromine, processes for the manufacture of these compounds and their use in pest control.

8 Claims, No Drawings

INSECTICIDAL 2,2-DIMETHYL-3-(2',2'-DIHALOVINYL)-CYCLOPROPANE CARBOXYLIC ACID 3-HALOPHENOXY-α-VINYLBENZYL ESTERS

RELATED APPLICATION

This is a continuation-in-part of application Ser. No. 084,954 filed Oct. 15, 1979, now abandoned.

The present invention relates to vinylcyclopropanecarboxylic acid 3-phenoxy-α-vinylbenzyl esters, processes for their manufacture, and their use in pest control.

The vinylcyclopropanecarboxylic acid 3-phenoxy-α-vinylbenzyl esters have the formula

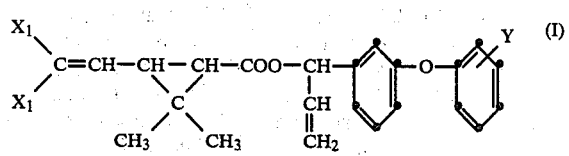

wherein each of $X_1$ and Y is fluorine, chlorine or bromine.

The compounds of the formula I are obtained by methods which are known per se, e.g. as follows:

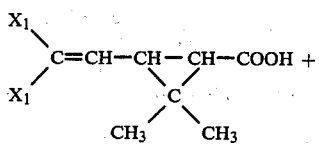

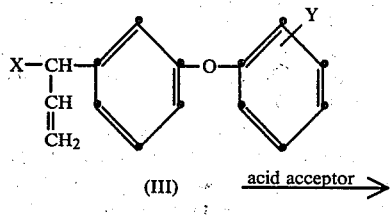

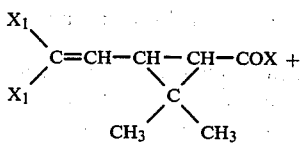

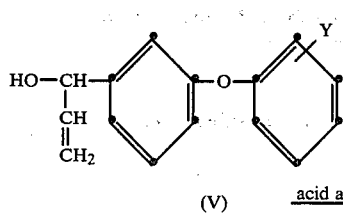

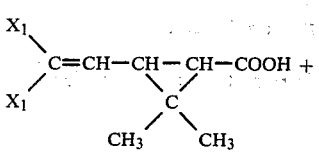

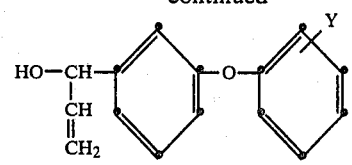

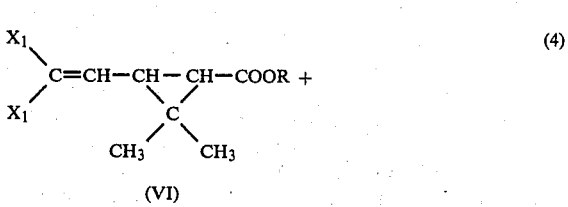

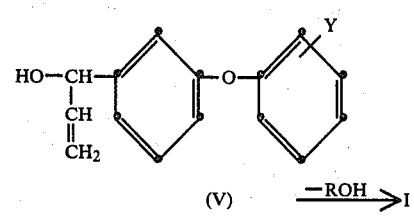

In the formulae II to VI, $X_1$ and Y are as defined for formula I.

X in formulae III and IV represents a halogen atom, especially a chlorine or bromine atom, and R in formula VI represents $C_1$-$C_4$ alkyl, especially methyl or ethyl.

Suitable acid acceptors for processes 1 and 2 are in particular tertiary amines, such as trialkylamine and pyridine, and also hydroxides, oxides, carbonates and bicarbonates of alkali metals and alkaline earth metals, and in addition alkali metal alcoholates, for example potassium tert-butylate and sodium methylate. As hydrophilic agent for process 3, it is possible to use e.g. dicyclohexylcarbodiimide. Process 1 to 4 are carried out at a reaction temperature between −10° and 120° C., usually between 20° and 80° C., under normal or elevated pressure and preferably in an inert solvent or diluent. Examples of suitable solvents or diluents are: ether and ethereal compounds, for example diethyl ether, dipropyl ether, dioxane, dimethoxyethane and tetrahydrofurane; amides, such as N,N-dialkylated carboxamides; aliphatic, aromatic and halogenated hydrocarbons, especially benzene, toluene, xylene, chloroform and chlorobenzene; nitriles, such as acetonitrile; dimethyl sulfoxide; and ketones, such as acetone and methyl ethyl ketone.

The starting materials of the formulae II, IV and VI are known and can be obtained by methods analogous to known ones. The compounds of the formula II are novel. They are obtained from the alcohols of the formula

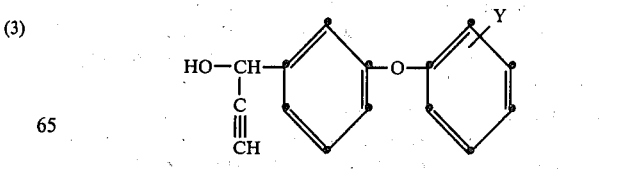

by reduction or from the aldehydes of the formula

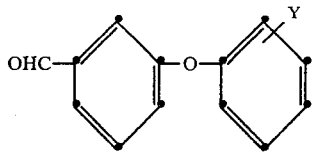

by Grignard reaction with X—Mg—CH=CH$_2$, wherein X is chlorine or bromine.

The compounds of the formula I exist in the form of a mixture of different optically active isomere if individual optically active starting materials are not used in the reaction. The different isomer mixtures can be separated into the individual isomers by known method. A compound of the formula I is to be understood as comprising both the individual isomers and the mixtures thereof. The compounds of the formula I are suitable for controlling a variety of animal and plant pests. In particular, the compounds of the formula I are suitable for controlling insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

In particular, the compounds of the formula I are suitable for controlling plant-destructive insects, especially plant-eating insects, in ornamentals and crops of useful plants, especially in cotton plantations (e.g. *Spodoptera littoralis* and *Heliothis virescens*) and in vegetable crops (for example *Leptinotarsa decemlineata* and *Myzus persicae*).

The active compound of the formula I are also very effective against flies, for example *Musca domestica* and mosquito larvae.

The compounds of the formula are also very effective against Lepidoptera that feed on keratin, for example Tineola spec. and Tinea spec., and also against Coleoptera that feed on keratin, for example Anthrenus spec. and Attagenus spec. The compounds are therefore very suitable for protecting keratinous material against attack by pests. They can be applied by the methods commonly employed in textile finishing and in particular provide such material with a wash- and lightfast protective finish against feeding damage by insects.

The keratinous material to be protected can be both in the raw and in the processed state, for example raw or processed sheep's wool, and products made of other animal hairs, hides, furs and feathers. In addition to the light- and washfast finish in the dyebath and in pad application, the compounds of the formula I can also be used for impregnating wool and woollen articles in dry cleaning, thereby also affording excellent protection against damage by eating.

In addition to their insecticidal action, the compounds of the formula I act against the larvae of the webbing clothes moth (*Tineola bisselliella*) and of the common clothes moth (*Tineola pellionella*) as well as against the larvae of the fur beetle and carpet beetle (Attagenus spec. and Anthrenus spec. respectively). The textiles, such as blankets, wool carpets, woollen underwear, woollen clothing and knits, are therefore protected against the common pests that feed on keratin. The materials to be protected also include blends, one component of which is wool, for example blends of wool and other natural fibres such as cotton, and of wool and synthetic fibres.

The acaricidal and/or insecticidal action can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, and chlorinated hydrocarbons.

Compounds of formula I are also combined with particular advantage with substances which exert a synergistic or potentiating effect on pyrethroids. Examples of such compounds include: piperonyl butoxide, propynyl ether, propynyl oximes, propynyl carbamtes and propynyl phosphates, 2-(3,4-methylenedioxyphenoxy)-3,6,9-trioxaundecane (Sesamex or Sesoxane), S,S,S,-tributylphosphorotrithioate, 1,2-methylenedioxy-4(2-(octylsulfinyl)-propyl)-benzene, N-(2-ethylhexyl)bicyclo-(2,2,1)-heptone(2)-2,3-dicarboximide.

The compounds of formula I may be used as pure active substance or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners, binders and/or fertilisers.

The compositions of the present invention are manufactured in known manner by homogeneously mixing and/or grinding active substances of the formula I with the suitable carriers, with or without the addition of dispersants or solvents which are inert to the active substances.

The compounds of formula I may be processed to the following formulations:
Solid formulations:
Dusts, tracking powders and granules (coated granules, impregnated granules and homogeneous granules).
Liquid formulations:
(a) active substances which are dispersable in water: wettable powders, pastes and emulsions;
(b) solutions.

The content of active substance in the above described compositions is generally between 0.1% and 95%, though concentrations of up to 99.5% or even pure active substance can also be used if the compositions are applied from an aircraft or other appropriate application devices.

The compounds (active substances) of the formula I can, for example, be formulated as follows (throughout the present specification all parts and percentages are by weight):
Dust:
The following substances are used to formulate (a) a 5% and (b) a 2% dust:

(a)

5 parts of active substance,
95 parts of talc;

(b)

2 parts of active substance,
1 part of highly disperse silicic acid,
97 parts of talc.
The active substance is mixed with the carriers and ground.
Granules:
The following substance are used to formulate 5% granules:
5 parts of active substance, 0.25 parts of epoxidised vegetable oil
0.25 parts of cetyl polyglycol ether,
3.50 parts of polyethylene glycol,
91 parts of kaolin (particle size 0.3–0.8 mm).

The active substance is mixed with epoxydised vegetable oil the mixture is dissolved in 6 parts of acetone; the polyethylene glycol and cetyl polyglycol ether are then added. The resultant solution is sprayed on kaolin, and the acetone is subsequently evaporated in vacuo.

Wettable powders:

The following constituents are used to formulate (a) a 40%, (b) and (c) a 25%, and (d) a 10% wettable powder:

(a)

40 parts of active substance,
5 parts of sodium dibutylnaphthalenesulfonate,
54 parts of silicic acid;

(b)

25 parts of active substance,
4.5 parts of calcium ligninsulfonate,
1.9 parts of Champagne chalk/hydroxyethyl cellulose mixture (1:1),
1.5 parts of sodium dibutylnaphthalenesulfonate,
19.1 parts of silicic acid,
19.5 parts of Champagne chalk,
28.1 parts of kaolin;

(c)

25 parts of active substance,
2.5 parts of isooctylphenoxy-polyoxyethylene ethanol,
1.7 parts of Champagne chalk/hydroxyethyl cellulose mixture (1:1),
8.3 parts of sodium aluminium silicate,
16.5 parts of kieselgur,
46 parts of kaolin;

(d)

10 parts of active substance,
3 parts of a mixture of the sodium salts of saturated fatty alcohol sulfates,
5 parts of naphthalenesulfonic acid/formaldehyde condensate,
82 parts of kaolin.

The active substance are homogeneously mixed with the additives in suitable mixers and the mixture is then ground in appropriate mills and rollers. Wettable powders are obtained which can be diluted with water to give suspensions of the desired concentration.

Emulsifiable concentrates:

The following substances are used to formulate (a) a 10%, (b) a 25% and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulfonate/calcium salt,
40 parts of dimethyl formamide,
43.2 parts of xylene;

(b)

25 parts of active substance,
2.5 parts of epoxidised vegetable oil,
10 parts of alkylarylsulfonate/fatty alcohol polyglycol ether mixture,
5 parts of dimethyl formamide, 57.5 parts of xylene;

(c)

50 parts of active substance,
4.2 parts of tributylphenol polyglycol ether,
5.8 parts of calcium dodecylbenzenesulfonate,
20 parts of cyclohexanone,
20 parts of xylene.

By diluting these concentrates with water it is possible to obtain emulsions of the required concentration.

Sprays:

The following ingredients are used to formulate (a) a 5% spray, and (b) a 95% spray:

(a)

5 parts of active substance,
1 part of epoxydised vegetable oil,
94 parts of ligroin (boiling range 160°–190°);

(b)

95 parts of active substance,
5 parts of epoxydised vegetable oil,

The invention is further illustrated by the following Examples.

EXAMPLE 1

(a) Manufacture of 3-(4-fluorophenoxy)-α-vinylbenzyl alcohol 145.3 g of 3-(4-fluorophenoxy)-α-ethynylbenzyl alcohol are dissolved in 1.5 liters of dioxane. To this solution are added 30 g of Lindlar catalyst. While shaking, 15.15 liters (105% of theory) of hydrogen are introduced into the mixture. The apparatus is then scavenged with nitrogen. The reaction mixture is filtered with suction and the solvent is removed by distillation, affording the alcohol of the formula

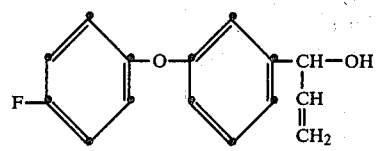

in the form of an oil with a refractive index of $n_D^{23°} = 1.5960$. The following alcohols are also obtained in analogous manner:

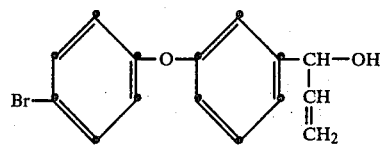

$n_D^{23.5°} = 1.6087$

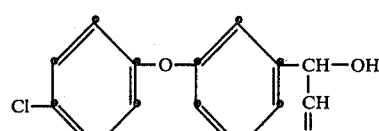

$n_D^{21°} = 1.5899$

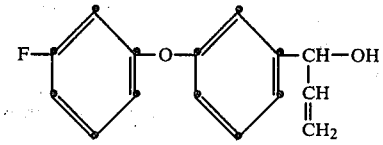

$n_D^{21°} = 1.5710$

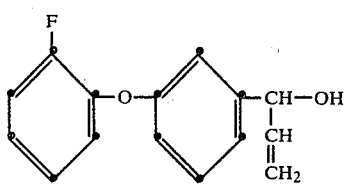

$n_D^{21°} = 1.5709$ (b) Manufacture of 2,2-dimethyl-3-(2,2-dichlorovinyl)-cyclopropanecarboxylic acid 3-(4-fluorophenoxy)-α-vinylbenzyl ester 2.4 ml of pyridine in 5 ml of toluene are added dropwise at 5° C. to a solution of 4.9 g of 3-(4-fluorophenoxy)-α-vinylbenzyl alcohol in 20 ml of toluene. Then 4.55 g of 2,2-dimethyl-3-(dichlorovinyl)-cyclopropanecarboxylic acid chloride (80%±cis, 20%±trans) are added dropwise at 10° C. The reaction mixture is then stirred for 2 hours at room temperature and allowed to stand for 12 hours. For working up, the reaction mixture is diluted with ice-water and the organic phase is extracted with three 100 ml portions of 3% hydrochloric acid solution and with three 100 ml portions of 3% sodium bicarbonate solution and the extracts are dried over sodium sulfate. The toluene is removed by distillation, affording the compound of the formula

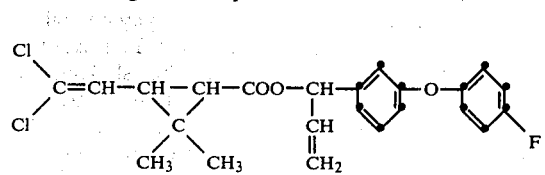

in the form of a colourless oil with a refractive index of $n_D^{40°} = 1.5488$; 100%±cis $N_D^{20°} = 1,5578$; 100%±trans $n_D^{20°} = 1,5564$.

The following compounds are also obtained in analogous manner:

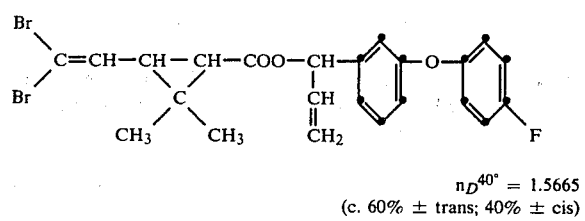

$n_D^{40°} = 1.5665$
(c. 60% ± trans; 40% ± cis)

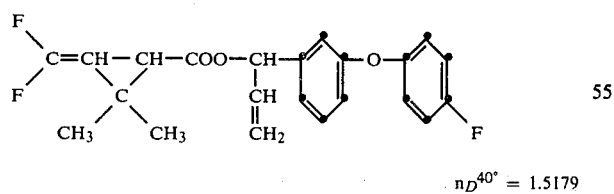

$n_D^{40°} = 1.5179$

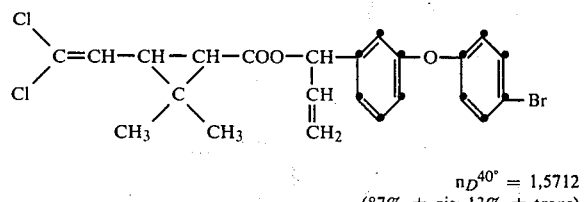

$n_D^{40°} = 1,5712$
(87% ± cis; 13% ± trans)

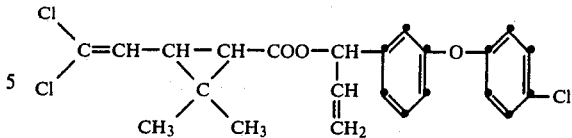

$n_D^{40°} = 1.5626$
(c. 60% ± trans; 40% ± cis)

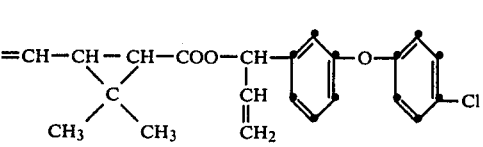

$n_D^{40°} = 1.5623$
(c. 87% ± cis; 13% ± trans)

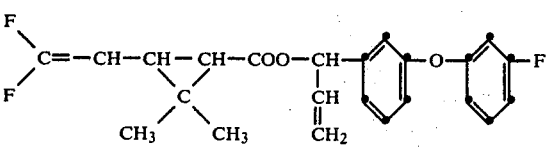

$n_D^{40°} = 1.5193$

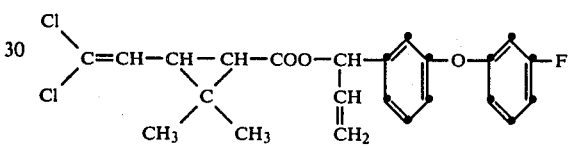

$n_D^{40°} = 1.5487$
(87% ± cis; 13% ± trans)

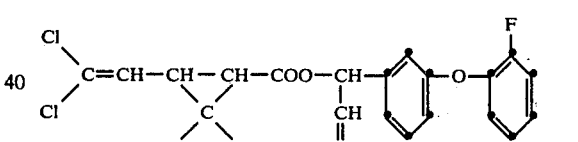

$n_D^{40°} = 1.5499$
(87% ± cis; 13% ± trans)

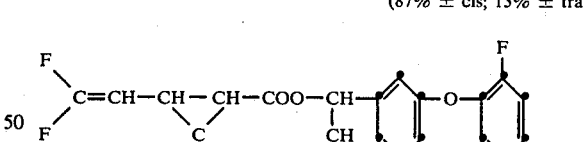

$n_D^{40°} = 1.5190$

EXAMPLE 2

Insecticidal stomach poison action

Cotton plants were sprayed with a 0.05% aqueous emulsion of active substance (obtained from a 10% emulsifiable concentrate). After the spray coating had dried, the cotton plants were populated with *Spodoptera littoralis* and *Heliothis virescens* in the L₃-stage. The test was carried out at 24° C. and 60% relative humidity.

In this test, the compounds of Example 1 exhibited a good insecticidal stomach poison action against Spodoptera and Heliothis larvae.

EXAMPLE 3

Acaricidal action

Twelve hours before the test for acaricidal action, *Phaseolus vulgaris* plants were populared with an infested piece of leaf from a mass culture of *Tetranychus urticae*. The mobile stages which had migrated to the plants were sprayed with the emulsified test preparations from a chromatography atomiser such that the spray broth did not run off. The number of living and dead larvae, adults and eggs was evaluated under a stereoscopic microscope after 2 and 7 days and the result expressed in percentage values. During the test run, the plants stood in greenhouse compartments at 25° C.

In this test, the compounds of Example 1 acted against adults, larvae and eggs of *Tetranychus urticae*.

EXAMPLE 4

Action against ticks (A) *Rhipicephalus bursa:* Five adult ticks and 50 ticks larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cotton wool plug and placed on its head to enable the cotton wool to absorb the active substance emulsion. Evaluation of the action against adults was made after 2 weeks and of that against larvae after 2 days. Each test was repeated twice.

(B) *Boophilus microplus* (*larvae*) Tests were carried out with 20 OP-sensitive and 20 OP-resistant larvae using aqueous emulsions similar to those used in Test A. (The resistance refers to the tolerance towards diazinone). The compounds of Example 1 were effective in these tests against adults and larvae of *Rhipicephalus bursa* and OP-sensitive and OP-resistant larvae of *Boophilus microplus*.

What is claimed is:

1. A compound of formula

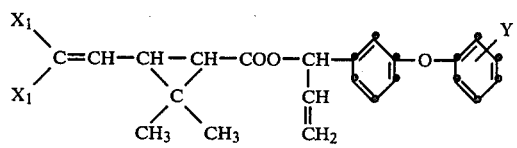

wherein each of $X_1$ and Y is fluorine, chlorine or bromine.

2. The compound according to claim 1 of the formula

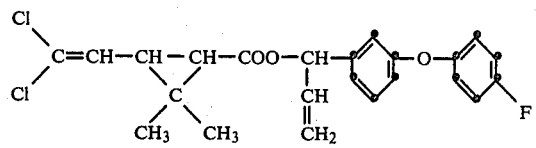

3. The compound according to claim 1 of the formula

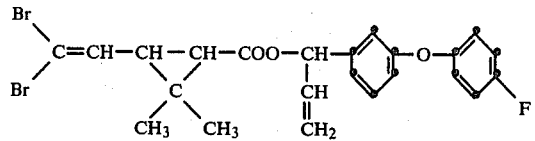

4. The compound according to claim 1 of the formula

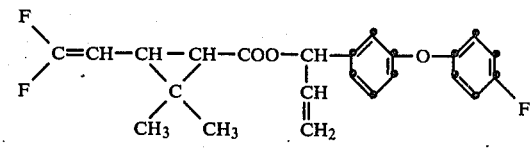

5. The compound according to claim 1 of the formula

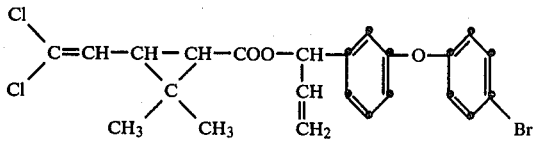

6. The compound according to claim 1 of the formula

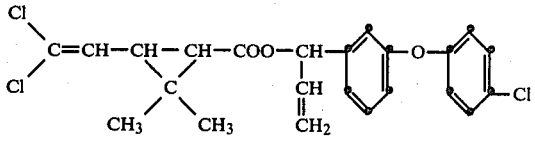

7. An insecticidal and acaricidal composition which contains, as active component, an insecticidally or acaricidally effective amount of a compound according to claim 1, together with a suitable carrier.

8. A method for controlling insects and acarids which comprises applying thereto an insecticidally or acaricidally effective amount of a compound according to claim 1.

* * * * *